(12) United States Patent
Chirica et al.

(10) Patent No.: US 8,911,606 B1
(45) Date of Patent: Dec. 16, 2014

(54) DIELECTROKINETIC CHROMATOGRAPHY DEVICES

(71) Applicant: Sandia Corporation, Albuquerque, NM (US)

(72) Inventors: Gabriela S. Chirica, Livermore, CA (US); Gregory J. Fiechtner, Germantown, MD (US); Anup K. Singh, Danville, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/050,502

(22) Filed: Oct. 10, 2013

Related U.S. Application Data

(62) Division of application No. 12/128,913, filed on May 29, 2008, now Pat. No. 8,702,946.

(60) Provisional application No. 60/941,083, filed on May 31, 2007.

(51) Int. Cl.
| | |
|---|---|
| *G01N 27/447* | (2006.01) |
| *G01N 27/26* | (2006.01) |
| *B01D 15/08* | (2006.01) |
| *B01D 63/00* | (2006.01) |

(52) U.S. Cl.
CPC .......... *G01N 27/44791* (2013.01); *B01D 15/08* (2013.01); *B01D 63/00* (2013.01)
USPC ..... 204/643; 204/547; 210/321.6; 210/198.2; 210/656; 422/68.1; 422/82.01; 435/287.1; 73/863.23

(58) Field of Classification Search
CPC . G01N 27/447; G01N 27/44791; B01D 63/00
USPC ........... 204/547, 643, 600; 210/321.6, 196.2, 210/656; 422/68.1, 82.01; 435/287.1
See application file for complete search history.

(56) References Cited

U.S. PATENT DOCUMENTS

| | | |
|---|---|---|
| 4,315,812 A | 2/1982 | Karlson |
| 4,563,516 A | 1/1986 | Schreckenberg et al. |

(Continued)

FOREIGN PATENT DOCUMENTS

| | | | |
|---|---|---|---|
| WO | WO 01/37958 A2 | 5/2001 | |
| WO | WO 2004/029221 | * | 4/2004 |

OTHER PUBLICATIONS

Cummings et al. (Anal. Chem. 2003, 75, 4724-4731).*

(Continued)

*Primary Examiner* — Jennifer Dieterle
(74) *Attorney, Agent, or Firm* — Smith, Gambrell & Russell, LLP

(57) ABSTRACT

Disclosed herein are methods and devices for dielectrokinetic chromatography. As disclosed, the devices comprise microchannels having at least one perturber which produces a non-uniformity in a field spanning the width of the microchannel. The interaction of the field non-uniformity with a perturber produces a secondary flow which competes with a primary flow. By decreasing the size of the perturber the secondary flow becomes significant for particles/analytes in the nanometer-size range. Depending on the nature of a particle/analyte present in the fluid and its interaction with the primary flow and the secondary flow, the analyte may be retained or redirected. The composition of the primary flow can be varied to affect the magnitude of primary and/or secondary flows on the particles/analytes and thereby separate and concentrate it from other particles/analytes.

12 Claims, 8 Drawing Sheets

(56) References Cited

U.S. PATENT DOCUMENTS

| | | | |
|---|---|---|---|
| 4,849,089 A | 7/1989 | Marshall, III | |
| 5,316,676 A | 5/1994 | Drori | |
| 5,376,279 A | 12/1994 | Judd et al. | |
| 5,427,663 A | 6/1995 | Austin et al. | |
| 5,454,472 A | 10/1995 | Benecke et al. | |
| 6,254,754 B1* | 7/2001 | Ross et al. | 204/548 |
| 6,310,309 B1 | 10/2001 | Ager et al. | |
| 6,428,666 B1 | 8/2002 | Singh et al. | |
| 6,603,054 B2 | 8/2003 | Chen et al. | |
| 6,641,708 B1 | 11/2003 | Becker et al. | |
| 6,824,664 B1 | 11/2004 | Austin et al. | |
| 7,005,301 B2 | 2/2006 | Cummings et al. | |
| 7,014,747 B2 | 3/2006 | Cummings et al. | |
| 7,204,923 B2 | 4/2007 | Cummings | |
| 7,264,723 B2 | 9/2007 | Singh et al. | |
| 7,344,681 B1 | 3/2008 | Fiechtner et al. | |
| 7,347,923 B2 | 3/2008 | Cummings et al. | |
| 7,419,574 B2 | 9/2008 | Cummings et al. | |
| 7,527,977 B1 | 5/2009 | Fruetel et al. | |
| 7,534,315 B1 | 5/2009 | Singh et al. | |
| 7,534,334 B1 | 5/2009 | Fiechtner et al. | |
| 7,602,307 B1 | 10/2009 | Brennan et al. | |
| 7,666,289 B2 | 2/2010 | Simmons et al. | |
| 7,678,256 B2* | 3/2010 | Davalos et al. | 204/547 |
| 7,713,395 B1* | 5/2010 | James et al. | 204/643 |
| 7,754,077 B1 | 7/2010 | Singh et al. | |
| 7,811,439 B1 | 10/2010 | Simmons et al. | |
| 7,828,948 B1 | 11/2010 | Hatch et al. | |
| 7,931,792 B2 | 4/2011 | Fiechtner et al. | |
| 7,999,937 B1 | 8/2011 | Srivastava et al. | |
| 8,047,829 B1 | 11/2011 | Sommer et al. | |
| 8,163,154 B1 | 4/2012 | Hatch et al. | |
| 8,257,568 B1 | 9/2012 | Simmons et al. | |
| 8,257,571 B1 | 9/2012 | Cummings et al. | |
| 8,329,016 B1 | 12/2012 | Sommer et al. | |
| 8,394,312 B1 | 3/2013 | Sommer et al. | |
| 8,518,346 B1 | 8/2013 | Chirica et al. | |
| 8,524,060 B1 | 9/2013 | Herr et al. | |
| 8,702,946 B1 | 4/2014 | Chirica et al. | |
| 8,703,058 B1 | 4/2014 | Hatch et al. | |
| 8,728,290 B1 | 5/2014 | Sommer et al. | |
| 2002/0175079 A1 | 11/2002 | Christel et al. | |
| 2003/0010637 A1* | 1/2003 | Cummings | 204/547 |
| 2004/0101481 A1 | 5/2004 | Hale et al. | |
| 2004/0107996 A1* | 6/2004 | Crocker et al. | 137/487.5 |
| 2004/0112751 A1 | 6/2004 | Han et al. | |
| 2004/0144651 A1 | 7/2004 | Huang | |
| 2005/0006293 A1 | 1/2005 | Koehler et al. | |
| 2005/0009101 A1* | 1/2005 | Blackburn | 435/7.1 |
| 2006/0163143 A1* | 7/2006 | Chirica et al. | 210/321.84 |
| 2006/0234379 A1 | 10/2006 | Lim et al. | |
| 2007/0084727 A1 | 4/2007 | Cummings | |
| 2007/0132230 A1 | 6/2007 | Mueller et al. | |
| 2010/0196941 A1 | 8/2010 | Braun et al. | |

OTHER PUBLICATIONS

Sandia Report, 2006, pp. 1-66.*

LabSmith HVS448 High Voltage Sequencer User Guide Version 1.4, 2011, pp. 1-77.*

Armstrong DW et al., "Determination of cell viability in single or mixed samples using capillary electrophoresis laser-induced fluorescence microfluidic systems," *Anal. Chem.* 2001;73:4551-7.

Armstrong DW et al., "Separating microbes in the manner of molecules. 1. Capillary electrokinetic approaches," *Anal. Chem.* 1999;71(24):5465-9.

Becker EW et al., "Fabrication of microstructures with high aspect ratios and great structural heights by synchrotron radiation lithography, galvanoforming, and plastic moulding (LIGA process)," *Microelec. Eng.* 1986;4:35-56.

Becker H et al., "Planar quartz chips with submicron channels for two-dimensional capillary electrophoresis applications," *J. Micromech. Microeng.* 1998;8(1):24-8.

Chirica G et al., "Silicate entrapped columns—New columns designed for capillary electrochromatography," *Electrophoresis* 1999;20:50-6.

Chirica G et al., "Size exclusion chromatography of microliter volumes for on-line use in low-pressure microfluidic systems," *Anal. Chem.* Aug. 1, 2006;78(15):5362-8.

Chirica GS et al., "A simple procedure for the preparation of fritless columns by entrapping conventional high performance liquid chromatography sorbents," *Electrophoresis* Sep. 2000;21(15):3093-101.

Chirica GS et al., "Fritless capillary columns for HPLC and CEC prepared by immobilizing the stationary phase in an organic polymer matrix," *Anal. Chem.* Aug. 1, 2000;72(15):3605-10.

Chirica GS et al., "Novel monolithic columns with templated porosity," *J. Chromatogr. A* Jul. 27, 2001;924(1-2):223-32.

Chou CF et al., "Sorting by diffusion: An asymmetric obstacle course for continuous molecular separation," *Proc. Nat'l Acad. Sci. USA* 1999;96(24):13762-5.

Cummings EB et al., "Dielectrophoresis in microchips containing arrays of insulating posts: Theoretical and experimental results," *Anal. Chem.* 2003;75:4724-31.

Cummings EB, "Streaming dielectrophoresis for continuous-flow microfluidic devices," *IEEE Eng. Med. Biol. Mag.* Nov.-Dec. 2003;22(6):75-84.

De Gasperis G et al., "Microfluidic cell separation by 2-dimensional dielectrophoresis," *Biomed. Microdevices* 1999;2(1):41-9.

Doneanu A et al., "Starburst dendrimers as macromolecular pore-templates for stationary phases in capillary chromatography," *J. Sep. Sci.* Nov. 2002;25(15-17):1252-6.

Han J et al., "Separation of long DNA molecules in a microfabricated entropic trap array," *Science* 2000;288:1026-9.

Huang LR et al., "A DNA prism for high-speed continuous fractionation of large DNA molecules," *Nat. Biotechnol.* 2002;20:1048-51.

Kreibik S et al., "Planar dielectrochromatography on non-wetted thin layers," *J. Planar Chromatography* Aug. 2001;14(4):246-51.

Lapizco-Encinas BH et al., "Dielectrophoretic concentration and separation of live and dead bacteria in an array of insulators," *Anal. Chem.* 2004;76:1571-9.

Lapizco-Encinas BH et al., "Insulator-based dielectrophoresis for the selective concentration and separation of live bacteria in water," *Electrophoresis* 2004;25:1695-704.

Lin IJ et al., "High-intensity, high-gradient electric separation and dielectric filtration of particulate and granular materials," *J. Electrostat.* 1982;13:257-8.

Sano H et al., "Dielectrophoretic chromatography with cross-flow injection," *Fifteenth IEEE Int'l Conf. on Micro Electro Mechanical Systems*, held on Jan. 20-Jan. 24, 2002 in Las Vegas, NV, pp. 11-14.

Suehiro J et al., "Dielectrophoretic filter for separation and recovery of biological cells in water," *IEEE Trans. Indus. Appl.* 2003;39(5):1514-21.

Svec F et al. (eds.), "Monolithic materials: Preparation, properties and applications," in vol. 7 of the *Journal of Chromatography Library*, 2003, Elsevier Science B.V., Amsterdam, The Netherlands, pp. XIII-XIX.

Tamaki E et al., "Nano chemical reactor," *Seventh Int'l Conf. on Miniaturized Chemical and Biochemical Analysis Systems*, held on Oct. 5-9, 2003, Squaw Valley, CA, pp. 681-684.

Throckmorton DJ et al., "Electrochromatography in microchips: Reversed-phase separation of peptides and amino acids using photopatterned rigid polymer monoliths," *Anal. Chem.* 2002;74:784-9.

IDEX Health & Science LLC, 2011-2012 Catalog "Fluidic products & information for laboratory applications," chapter entitled "Filters & frits," pp. 156-172 (available at http://www.idex-hs.com/about/data_sheets/Catalog_Complete_np.pdf, last accessed Jul. 2, 2014).

Wang HY et al., "Electroporation of mammalian cells in a microfluidic channel with geometric variation," *Anal. Chem.* 2006;78-5158-64.

Zhou G et al., "A dielectrophoretic filter for separation and collection of fine particles suspended in liquid," *Conf. Record of the Seventh IAS Annual Meeting of Industrial Applications*, held on Oct. 13-18, 2002 in Pittsburgh, PA, vol. 2, pp. 1404-1411.

Zhou R et al., "CdSe nanowires with illumination-enhanced conductivity: Induced dipoles, dielectrophoretic assembly, and field-sensitive emission," *J. Appl. Phys.* 2007;101;073704 (9 pp.).

* cited by examiner

1st Dimension Chromatography

2nd Dimension Dielectrophoresis

Detection

HV

Trapped Fluospheres

DIELECTROKINETIC CHROMATOGRAPHY DEVICES

CROSS REFERENCE TO RELATED APPLICATIONS

This application is a divisional application of utility U.S. patent application Ser. No. 12/128,913 entitled "DIELECTROKINETIC CHROMATOGRAPHY AND DEVICES THEREOF", filed on May 29, 2008, which claims priority to and the benefit of the filing of provisional U.S. Patent Application Ser. No. 60/941,083 entitled "DIELECTROKINETIC CHROMATOGRAPHY AND DEVICES THEREOF", filed on May 31, 2007. Both of the aforementioned applications are incorporated herein by reference.

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

BACKGROUND OF THE INVENTION

1. Field of the Invention

The present invention generally relates to microfluidic and nanofluidic analysis of analytes. In particular, the present invention relates assaying analytes based on their mobilization characteristics in applied mobilization fields.

2. Description of the Related Art

Separation by size or mass is a fundamental analytical and preparative technique in biology, medicine, chemistry, and industry. Conventional methods include gel electrophoresis, capillary electroosmotic chromatography (CEC), field-flow fractionation, sedimentation and size exclusion chromatography (SEC).

A few microfluidic and nanofluidic devices for separation and analysis of biomolecules and compounds have been developed. U.S. Pat. No. 5,427,663 discloses separating nucleic acid molecules using electric fields through an array of posts as sieving matrices. Chou et al. (Proceedings of the National Academy of Science, USA, 1999, v. 96:13,762) disclose sorting nucleic acid molecules according to their diffusion coefficients using an electric field which propels the molecules through gaps formed by an asymmetric array of objects. Han and Craighead (Science, 2000, v. 288:1026-1029) disclose separations using entropic traps consisting of a series of many narrow constrictions (<<100 nm) separated by wider and deeper regions (a few microns). Huang et al. (Nature Biotechnology, 2002, v. 20:1048) disclose a hexagonal array of posts which act as a sieving matrix in pulsed-field electrophoresis. Published U.S. Patent Application 20040144651 discloses an array of obstacles wherein molecules are separated according to size. Unfortunately, the arrays required for providing patterned field non-uniformities suitable for assaying analytes is costly and impracticable for processing real world samples.

Similarly, various attempts to assay intact bacteria viruses in real world samples using capillary electrophoresis (alone) had limited success due to the relative low concentration of cells in the samples. See Armstrong et al. Analytical Chemistry, 1999, v. 71:5465, and Armstrong et al. Analytical Chemistry, 2001, v. 73:4551. Methods to select and/or concentrate cells are needed to improve detection sensitivity in real world samples.

Dielectrophoresis, on the other hand, enables trapping and concentration of particulates in non-uniform electric fields. For example, the Washizu group in Japan used arrays of embedded electrodes to separate latex particles (100 nm and 1 $\mu$m in diameter) and DNA particulates purely based on dielectrophoretic effects. See Sano et al. Institute of Electrical and Electronics Engineers, Transactions of Industry Applications, 2002, v. 11. The Washizu group calls this technique dielectrophoretic "chromatography"; however, the separation is solely due to dielectric effects and no chromatography, i.e. adsorption, desorption mechanism, is involved.

Lin et al. (Journal of Electrostatics, 1982, v. 13:257) use dielectric filtration and high-gradient electric separation induced by a dielectric body (e.g. ceramic beads) in a uniform electric field to remove particulates in large-scale industrial applications suitable for liquids with low conductivity. Suchiro et al. (Institute of Electrical and Electronics Engineers, Transactions of Industry Applications, 2003, v. 39:1514) use two parallel plate electrodes to create non-uniform electric field gradients. Se also Zhou et al., Institute of Electrical and Electronics Engineers, Transactions of Industry Applications, 2002, v. 2:1404.

Unfortunately, devices with embedded electrodes or devices with dielectric particulates are difficult, expensive and hard to manufacture reproducibly especially for microliter volume applications. In addition, integration in a complex multifunctional system is challenging due to inherent band broadening effects that occur during transition from chip to other processing and/or detection devices. Due to the small size of microfluidic devices, localized surface modification with application specific chemical groups is extremely difficult, as is the control of surface porosity. Such limitations on surface characteristics render embedded electrode-based devices unsuitable for chromatographic applications and nanodielectrophoretic experiments.

Kreibik et al. (Journal of Planar Chromatography, 2001, v. 14:246) introduced a technique, "planar dielectrochromatography", which uses non-linear effects generated by alternating currents to pump liquids through a planar thin layer of chromatographic plate to developed distinctive spots of dyes; the plate system has very low sensitivity and has limited applicability as it is not suitable for high-throughput high-sensitivity methods required in bioanalysis.

There is therefore a need for economical microfluidic devices and methods which are easy to fabricate and use for rapidly processing and assaying particulates in fluid samples.

SUMMARY

The present invention provides methods and devices for assaying or processing an analyte in a fluid sample which comprises subjecting the analyte to an electrokinetic flow field and a dielectrophoretic flow field produced by at least one field non-uniformity resulting from a plurality of randomly arranged perturbers in a perturber section. Moreover, by judicious selection of the surface chemistry of the perturbers and by variations in the composition of the fluid a chromatographic separation dimension is superimposed on the dielectrophoretic separation effect. Lastly by using perturbers of small dimension, i.e., tens of micrometers and smaller, one can manipulate nanometer sized particles suspended in the fluid.

Both the foregoing general description and the following detailed description are exemplary and explanatory only and are intended to provide further explanation of the invention as claimed. The accompanying drawings are included to provide a further understanding of the invention and are incorporated in and constitute part of this specification, to illustrate several embodiments of the invention, and together with the description serve to explain the principles of the invention.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF EMBODIMENTS OF THE INVENTION

Figure 1:
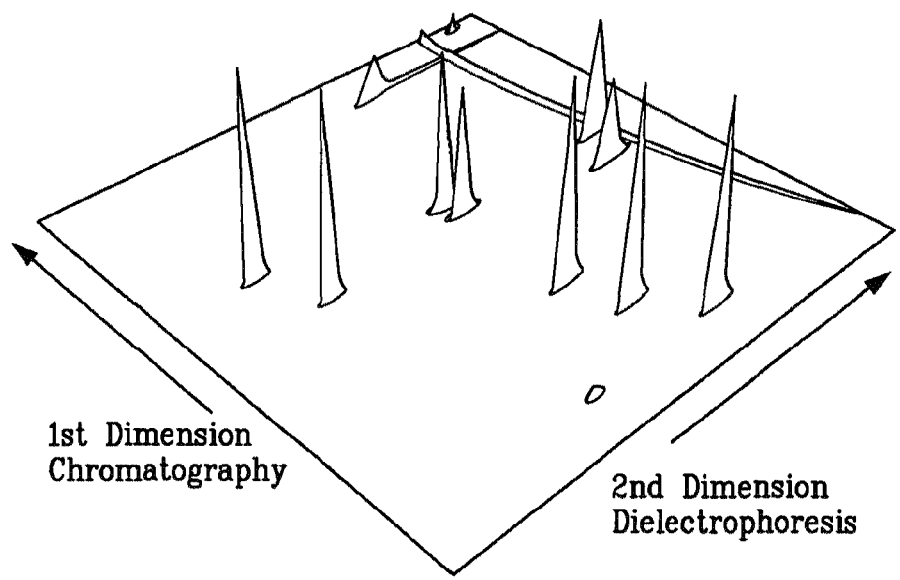
FIG. 1 is a symbolic representation of dielectrokinetic chromatography according to the present invention.

As provided herein, the present invention provides methods and devices for processing and/or separating analytes in a fluid using dielectrokinetic chromatography (DEKC) in a channel, preferably a microchannel. As used herein, "channel" refers to a structure wherein a fluid may flow and includes a capillary, a conduit, a strip of hydrophilic pattern on an otherwise hydrophobic surface wherein aqueous fluids are confined, and the like. In some embodiments, the channel is a capillary. As used herein, "microfluidic" refers to a system or device having one or more fluidic channels, conduits or chambers that are generally fabricated at the centimeters to nanometer scale. Thus, the "microfluidic channels" or alternatively referred to herein as "microchannels" of the present invention generally have cross-sectional dimensions ranging from about 10 nm to about 1 cm, preferably about 1 mm to about 50 mm, more preferably about 1 mm to about 25 mm, in diameter and about 1 mm to about 100 cm, preferably about 1 cm to about 75 cm, more preferably about 2 cm to about 50 cm, most preferably about 2 cm to about 10 cm, in length.

As used herein, a "fluid" refers to a substance that tends to flow and to conform to the outline of a container such as a liquid or a gas. Fluids include saliva, mucus, blood, plasma, urine, bile, breast milk, semen, tears, water, liquid beverages, cooking oils, organic solvents, hydrocarbon oils, fluorocarbon oils, ionic fluids, air, and the like and mixtures thereof. Fluids can also exist in a thermodynamic state near the critical point, as in supercritical fluids. If one desires to test a solid sample for a given analyte according to the present invention, the solid sample may be made into a fluid sample using methods known in the art. For example, a solid sample may be dissolved in an aqueous solution, ground up or liquefied, dispersed in a liquid medium, melted, digested, and the like. Alternatively, the surface of the solid sample may be tested by washing the surface with a solution such as water or a buffer and then testing the solution for the presence of the given analyte.

As used herein, an "analyte" may be a natural or synthetic chemical or a natural or synthetic biological entity. Chemicals and biological entities (e.g. biomolecules) include industrial polymers, powders, latexes, emulsions, colloids, environmental pollutants, pesticides, insecticides, drugs such as cocaine and antibiotics, magnetic particles, high magnetic-permeability particles, metal ions, metal ion complexes, inorganic ions, inorganic oxides, inorganic ion complexes, organometallic compounds, metals including aluminum, arsenic, cadmium, chromium, selenium, cobalt, copper, lead, silver, nickel, and mercury, and the like, amino acids, peptides, proteins, glycoproteins, nucleotides, nucleic acid molecules, carbohydrates, lipids, lectins, cells, viruses, viral particles, bacteria, organelles, spores, protozoa, yeasts, molds, fungi, pollens, diatoms, toxins, biotoxins, hormones, steroids, immunoglobulins, antibodies, supermolecular assemblies, biomolecular polymers, ligands, catalytic particles, zeolites, and the like, biological and chemical warfare agents, agents used in explosives, and the like.

As used herein, "separating" is used interchangeably with "sorting", "fractionating", "resolving", "collecting", "concentrating", "filtering", "assaying", "detecting", "measuring", "monitoring", and "analyzing". As provided herein, analytes are separated by DEKC, a process in which analytes are made to depart from a primary flow via a secondary flow either longitudinally, thereby resulting in a modified spatial distribution of the analytes in a channel. As used herein, "processing" includes separating and methods known in the art which are employed to manipulate, modify, or change a given analyte, e.g. lysing or porating a cell or chemically modifying an analyte.

Specifically, the present invention provides methods and devices which separate analytes based on one or more characteristics by competing a primary flow field (e.g. a primary mobilization field) with a secondary flow field (e.g. a secondary mobilization field) in a fluid channel. As used herein, "mobilization field" refers to any force field that influences an analyte to pass through a channel or region of a channel. Mobilization fields include hydrodynamic flow fields produced by pressure differences, gravity, linear or centripetal acceleration, electrokinetic flow fields, electroosmotic flow fields, magnetophoretic and thermophoretic flow fields, electric fields, optical fields, centrifugal fields, gravitational fields, combinations thereof, and the like.

The primary flow is the motion of analytes (flow) resulting from a primary flow force exerted by the primary flow field. Primary flow is generally in a direction that is substantially parallel to the boundaries of a microchannel. As used herein, a "primary flow force" is the force on an analyte that makes it follow the primary flow. Two classes of primary flow are considered herein, "hydrodynamic flows" which, as used herein, include pressure-gradient-, capillarity-, inertia-, gravity, centripetal acceleration-, chemical reaction-, and magnetically-driven flows and the like and "electrokinetic" flows which are the superposition of electrophoretic and electroosmotic flows. The electrokinetic flows considered herein can have substantial electrophoretic and electroosmotic components or have substantially dominant electrophoretic or electroosmotic components either by the choice of channel boundaries, fluid composition, surface treatments, surfactants, dynamic coatings, gels, etc. as is well known in the art.

The secondary flow field retains or redirects analytes from the primary flow. The secondary flow field is produced by mechanical interactions, inertial interactions, entropic interactions, electrostatic interactions, magnetic interactions, electromagnetic interactions, optical interactions, chemical interactions, or by combinations thereof; and further includes at least one field non-uniformity projected or produced from patterns in the channel.

Secondary flow generally refers to the motion of an analyte resulting from its interactions with forces produced by the secondary flow field and the "secondary flow force" refers to the force that produces the secondary flow. The secondary flow in the present invention is produced by interactions that occur substantially throughout the cross-section of the primary flow at a region or regions in the channel and are referred to as "volume interactions". As used herein, "volume interaction" refers to any force on an analyte that the analyte can experience substantially throughout the cross-section of a flow channel. Thus, "secondary flow" is the analyte motion produced by volume interactions resulting from at least one spatially non-uniform field within the flow channel.

Volume interactions are different from "surface interactions", which occur only when an analyte is in immediate proximity to a channel boundary. As used herein, "surface interaction" refers to any force on an analyte that it experiences in immediate proximity to the surface of the channel or a substrate in the channel. Such surface interactions include Van der Waals and other "adhesive" forces, chemical interactions, electrostatic forces within a Debye layer that is thin compared other channel dimensions, steric effects and mechanical reaction forces produced when analytes are forced onto or collide with a surface, and the like. Generally, these surface interactions are not employed to produce a secondary flow according to the present invention. However, surface interactions are employed to affect or influence the balance between the primary and secondary forces on analytes and add another separation mode to assay different particulates a sample. As provided herein, the present invention combines "surface interactions" and "volume interactions" to improve the resolving power of microfluidic separations.

As used herein, "a field non-uniformity" refers to a spatial gradient in a field. As provided herein, a field non-uniformity is produced within the channel by a plurality of perturbers which are discrete bodies randomly packed or spaced from each other (i.e., non-coherent). As used herein, a "perturber" distorts an applied flow, an electric field, or the action of an area or region in a channel which produces gradients in an intrinsic field, e.g., the electric field within the Debye layer. Perturbers of the present invention may be made of material that is the same as or different from the material defining the microfluidic channel in which it is located. Suitable materials for the perturbers include materials that are insulative, conductive, semi-conductive, or a combination thereof. The surface chemistries and surface pore chemistries of the perturbers according to the present invention may be the same or different from the microfluidic channel in which it is located. As provided herein, a "perturber section" refers to a section of a microfluidic channel that contains a plurality of perturbers which are randomly packed or spaced from each other. In some embodiments, the perturber section may be adjacent to or in fluidic communication with a portion of a microfluidic channel that does not contain perturbers. In some embodiments, the perturber section may be adjacent to or in fluidic communication with a second perturber section which may contain perturbers which are the same or different from the perturbers in the first perturber section.

As used herein, the word "conductivity" is used to describe the ease of flow of both conduction and displacement current. It is often mathematically described as a complex number that varies with the frequency of an applied electric field. Similarly, "conduction" is used to describe both conventional conduction and conduction of displacement currents. As used herein, "insulative" and "conductive" refers to the relative conductivity of the described item with respect to the fluid.

Insulative materials have relatively low conductivity and include plastics, epoxies, photoresists, polymers, silicon, silica, quartz, glass, controlled pore glass, carbon, and the like, and combinations thereof, such as thermoplastic polymers such as nylon, polypropylene, polyester, polycarbonate, and the like. Conductive materials, in comparison, have relatively high conductivity. Conductive materials include bulk, sputtered, and plated metals and semiconductors, carbon nanotubes, and the like.

The devices of the present invention are readily fabricated using methods known in the art including techniques conventionally used for silicon-based integrated circuit fabrication, embossing, casting, injection molding, silica capillaries, and the like. See e.g. Becker, et al., Microelectronic Engineering, 1986, v. 4:35-56, which is herein incorporated by reference. Other suitable fabrication techniques include photolithography, electron beam lithography, imprint lithography, reactive ion etching, wet etch, laser ablation, embossing, casting, injection molding, and the like. See e.g. Becker, et al., Microelectronic Engineering, 1998, v. 8:24-28, which is herein incorporated by reference.

In some embodiments, the methods and devices of the present invention employ fused silica capillaries coated with a polymer such as polyimide, polytetrafluoroethylene, and the like. In some embodiments, the methods and devices of the present invention employ fittings such as tees, unions, ferrules, and the like. Such capillaries and fittings are known in the art or commercially available.

The devices of the present invention may be fabricated from materials that are compatible with the conditions present in the particular application of interest. Such conditions and considerations include pH, temperature, application of organic solvents, ionic strength, pressure, application of electric fields, surface charge, sticking properties, surface treatment, surface functionalization, bio-compatibility, and the like. The materials of the devices may be chosen for their surface chemistry, bulk/based material chemistry, geometry, porosity, optical properties, magnetic properties, mechanical properties, and for their inertness to compounds to be exposed thereto, and the like. Such materials include glass, fused silica, silicone rubber, silicon, ceramics, polymers, and the like.

In some embodiments, analytes are unloaded from the device using methods known in the art, including microfluidic channels at the end of a perturber section and are then be routed for further use. In particular, binning channels may be employed to divert a fluid stream of interest to another perturber section, a detection area for observation or visualization, to a reaction area or another device for further manipulations including chemical and physical reactions, and the like. In some embodiments, a plurality of perturber sections which contain the same or different perturbers may be used in series or parallel, or a combination thereof to process and/or separate different analytes in a sample or samples. In some embodiments, more than one type of perturber may be used in a given perturber section. For example, mixtures of perturbers having different properties may be placed in one capillary.

Embodiments diagrammed herein show the active regions of the channels and/or show only some the structural features for collecting analytes, flushing, cleaning, elution, and the like. Thus, it should be noted that the devices of the present invention may further comprise multiple ports, offset-t structures, electrodes, and other microfluidic structures and means known in the art for implementing sample introduction, manipulation, analysis and detection. Moreover, the embodiments diagrammed herein do not show comprehensively the external apparatus for providing the primary flow field and the secondary flow fields.

In some embodiments, portions of the devices of the present invention are optically transparent such that optical detection methods known in the art, including fluorescence detection and imaging using inverted-optic microscopes, may be used. In some embodiments, the fluid flows and separations are monitored in real-time. In some embodiments, the exterior of the devices are constructed such that interfaces, including capillary ports, and the like, known in the art may be conveniently and reliably accommodated.

In some embodiments, the channels of the devices are constructed with materials and dimensions that exhibit low intrinsic fluorescence. Thus, in some embodiments, the substrate of the devices comprises fused silica as fused silica exhibits low intrinsic fluorescence. In some embodiments, the devices comprise binning channels for post-separation analysis or further manipulations.

Devices can be constructed from a sandwich of two or more substrates so that channels are bounded conduits with ports. Bonding of the substrates may be done using methods known in the art including thermal bonding of nanofluidic channels in fused silica. See e.g. Tamaki, et al., Proceedings of MicroTotal Analysis Systems, 2003, v. 1:681, which is herein incorporated by reference. Devices can be constructed by bonding bundles of capillaries together.

DEKC devices may be combined with other devices that employ separation methods known in the art including microcolumn-based, capillary-based or on-chip chromatography, such as electrochromatography (see Singh, Analytical Chemistry, 2002, v. 74:784-789, which is herein incorporated by reference), micellar electrokinetic chromatography, or reverse-phase high pressure liquid chromatography, and the like, as well as sample preparation methods, chemical processing methods, and biological methods known in the art. The DEKC devices of the present invention may be combined with other devices that are used to interface separating and/or processing devices with a detection device. For example, a DEKC device of the present invention may be combined with capillaries which directly interface with a mass spectrometer. Various geometries and device configurations may, according to the present invention, be readily designed by one skilled in the art for desired versatility and performance.

Dielectrokinetic Chromatography (DEKC)

The present invention provides methods and devices for DEKC for rapidly separating, concentrating, and assaying analytes. In particular, DEKC is a two-dimensional separation method where the first dimensional separation is chromatography which separates analytes through surface interactions and the second dimensional separation is dielectrophoresis (DEP) which separates analytes volumetrically using field non-uniformities caused by perturbers. Thus, the primary flow field can be hydrostatic, electrokinetic, electrophoretic or a combination thereof and the secondary field is preferably a dielectrophoretic field. The electrokinetic field and the dielectrophoretic field may be applied separately or simultaneously, continuously or for selected time intervals during the separation.

As disclosed herein, the methods and devices for DEKC may employ fluidic channels, capillaries and columns known in the art. This invention shows that fluidic channels, capillaries or columns packed with particles of a given shape and size can be used for dielectrophoretic trapping since the particles themselves act as perturbers of electric field. As a result, DEKC according to the present invention can be readily applied to existing columns and/or instruments that are currently used for separations. In some embodiments, the methods and devices for DEKC employ chromatography columns known in the art, such as Agilent Technologies, Inc. (Santa Clara, Calif.), Michrom Bioresources, Inc. (Oak Harbor, Wash.), Waters (Milton, Mass.), New Objective (Woburn, Mass.), and Labsmith (Livermore, Calif.). The dimensions of the channels, capillaries and columns may be readily selected by those skilled in the art in accordance with the present invention.

Generally, the devices for DEKC (DEKC devices) comprise perturbers bodies of a desired shape and size packed in a perturber section. The shape of the perturbers may be any desired shape such as spherical, regular or irregular shaped, porous or non-porous, with a non-porous core and a porous surface, tubular, and the like. Perturbers according to the present invention also include structures within monolithic columns, porous polymer rods, and the like. In some embodiments, the perturbers are porous or nonporous spheres made of methacrylate, borosilicate glass or silica. The size of the perturbers may be any useful size. In some embodiments, the diameter of the perturbers range from about 20 µm to about 30 µm. In some embodiments, the diameter of the perturbers ranges from 1:7 to 1:2 of the cross-sectional area of the perturber section in which they are contained. In some embodiments, the perturbers in the perturber section are of the same or substantially similar sizes. In some embodiments, the perturbers in the perturber section are of various sizes and/or composition. In some embodiments, the shape of the perturbers in the perturber section are the same or substantially similar. In some embodiments, the perturbers in a perturber section are of various shapes.

The perturbers in the perturber section may be made from a wide variety of materials including silica, borosilicate glass, methacrylate, polyacrylamide, polystyrene divinylbenzene, dextrose, latex, zirconium and aluminum oxide, magnetic beads with derivatized surfaces, metal-based beads, ceramic beads, and the like. In some embodiments, the perturbers are made of silica, methacrylate, or latex.

Electrokinetic field and the dielectrophoretic field may be induced by applying a voltage across the perturber section using a variable high voltage power supply, typically a programmable power supply, such as is known in the art. Under an applied voltage, the perturbers in the perturber section generate multipoint electric field gradients which induce streaming or trapping of analytes present in a fluid sample. One skilled in the art may readily tune or optimize the multipoint electric field gradients by selecting of the exterior structure, geometry and/or chemistry of the perturbers, the internal porosity of the perturbers and their electrical and/or magnetic properties, and the like.

As described herein, perturbers in the shape of spheres were packed in a microchannel and a fluid sample having analytes was passed through the microchannel. The perturbers were borosilicate glass, dry lime soda microspheres from Duke Scientific (Microgenic Corporation, Fremont, Calif.) and polystyrene microspheres from Bangs Laboratories (Fishers, Ind.). The analytes were fluorescently labeled carboxylate-modified microspheres (e.g. FLUOSPHERES® obtained from Molecular Probes Inc., Eugene, Oreg., a division of Invitrogen Inc., Carlsbad Calif.). Under an applied voltage, the analytes were observed to become concentrated at a given location.

Also, as described herein, the spheres (i.e., perturbers) were packed in a capillary and a fluid sample having analytes was passed through the packed capillary. The perturbers were borosilicate glass, dry lime soda microspheres from Duke Scientific (Microgenic Corporation, Fremont, Calif.) and polystyrene microspheres from Bangs Laboratories (Fishers, Ind.). The analytes were fluorescently labeled carboxylate-modified microspheres (e.g. FLUOSPHERES® obtained from Molecular Probes Inc., Eugene, Oreg., a division of Invitrogen Inc., Carlsbad Calif.) or *Bacillus subtilis* spores. Under an applied voltage, the analytes were observed to become concentrated at a given location.

FIG. 1 represents DEKC according to the present invention. As depicted in FIG. 1, the use of electrokinetic fields and dielectrophoresis fields can improve the separation between the peaks since two orthogonal separation methods (i.e. the separation mechanisms are completely distinct and act independently) are employed to cause differential migration of analytes. The ability to baseline-separate or resolve more analytes translates into higher peak capacity (#peaks resolved by 2D method=#peaks resolved by method 1×#of peaks resolved by method 2). Since a large number of perturbers are used, the DEKC methods and devices according to the present invention generate a large number of gradient-field points and thereby substantially increases sample capacity over that of prior art methods. As provided herein, DEKC exploits the selectivity of chromatography and the volumetric attraction and repulsion to field non-uniformities resulting from dielectrophoresis which provides high sample capacity and high resolution separations needed for assaying analytes on the nanoscale and microscale. Rapid separations and high resolution of the proposed system ultimately enable high throughput analysis of analytes.

Figure 2:
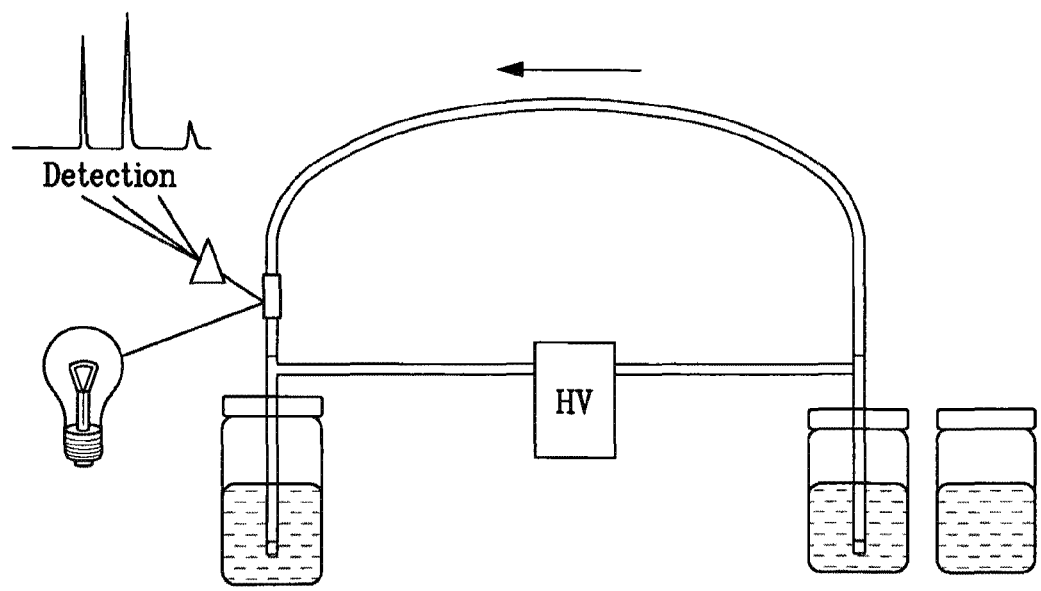
FIG. 2 is a schematic representation of a device arrangement commonly used for capillary electrochromatography. This arrangement along with fluorescent imaging and slightly pressurizing the sample vial was used for the dielectrokinetic chromatography methods disclosed herein.

Traditional chromatographic formats use pressure-driven flow to pass the analytes through the separation column. The parabolic profile characteristic of hydraulic flow introduces significant peak broadening (10,000 plates/m) and therefore diminishes resolution analytes. This problem of peak broadening may be reduced by using an electrokinetic flow field for inducing the primary flow of a fluid sample. For example, in capillary electroosmotic chromatography (CEC), an electric field is applied across a packed capillary to generate electroosmotic transport of the mobile phase and analytes as shown in FIG. 2. Narrower peaks (100,000 plates/m) are obtained by this approach than by pressure-driven flow methods since the flat electroosmotic (electrokinetic) flow profile yields less peak broadening.

As described herein, the DEKC methods and devices may employ any mode of chromatography such as reverse phase, ionic interactions, affinity interactions, and the like. Thus, DEKC methods and devices may be used to separate macromolecular complexes, nanoscale molecules and other nano-to-micrometer size particulates.

Figure 3A:
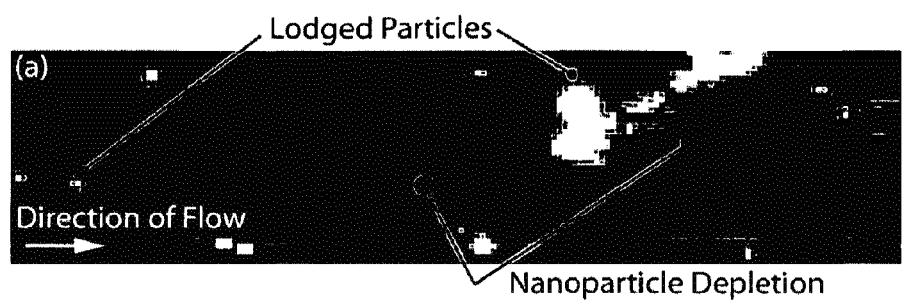
FIG. 3A illustrates nanodielectrophoresis in the form of depletion/rarefaction of nanometer sized particles achieved by using micrometer sized perturbers packed in a perturber section, in this case between the walls of a microchannel or capillary.
Figure 3B:
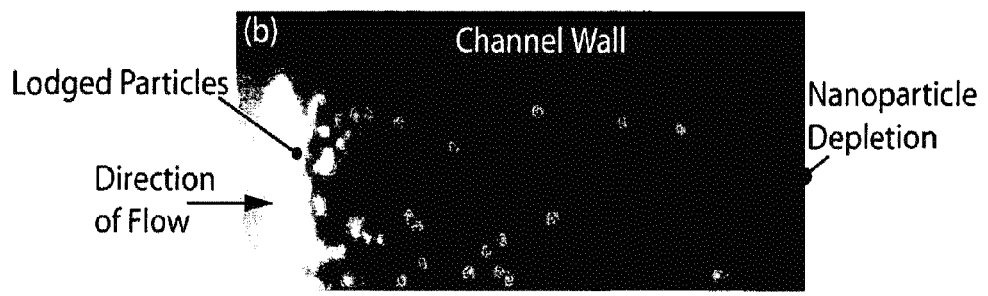
FIG. 3B is a fluorescent image which shows rarefaction of nanometer size analytes present in the surrounding fluid due to dielectrophoretic trapping adjacent to perturbers packed/lodged in a perturber section.

To demonstrate that the smaller the perturber, the smaller the size of analytes one can concentrate by using dielectrophoresis, a suspension of fluorescently labeled polystyrene microspheres of about 100-nm in diameter (analytes) FLUOSPHERES® (obtained from Molecular Probes Inc., Eugene, Oreg., a division of Invitrogen Inc., Carlsbad Calif.) was flowed through a microchannel with a primary electrokinetic flow field. See FIG. 3A. The microchannel contained "bumps" (large perturbers) imprinted in the microchannel by design with about a 5 µm gap between the bump surface and the top wall of the microchannel and small perturbers, e.g., microspheres having diameters of about 1 µm, lodged on channel surfaces within the gap. Under applied voltages of about 100 V/mm, local rarefaction of analytes was observed as the analytes flowed around the spheres packed in the microchannel. Small analytes were not trapped by the large perturbers since the electric field gradients were not steep enough due to their size. As shown in FIG. 3A, the decrease in fluorescence intensity, which is characteristic of dielectrophoretic depletion, is observed at a number of locations in the microchannel, and appear as dark streaks as the analytes flow from left to right. This provides evidence that the secondary flow field DEP, may be induced by applied voltages falling within the ranges suitable for inducing electrokinetic flow fields. In particular, the secondary flow field can be optimized by employing geometrical features to trap small size analytes. FIG. 3B shows another separation where agglomerated clumps of analytes (evidenced by fluorescently labeled microspheres) become concentrated on or near the surfaces of a 900-nanometer gap between a ridge and the channel cover. The resulting flow shows depletion and concentration of about 100 nm analytes.

The strength of the dielectrophoretic effect indicates that smaller analytes can be impacted/trapped or that the field magnitude is large enough to affect their motion, depending on field strength and the curvature of the lodged perturbers. That is, the larger the curvature, the steeper the electric field gradients generated by the perturber. For optimum electrokinetic flows, such rarefaction due to analyte motion affected by the field (resulting in deflection at lower fields to trapping at stronger fields) is not possible and the presence of rarefaction is direct evidence of nonlinear electrokinetic effects (e.g. electrohydrodynamic), likely to be multigradient dielectrophoresis (multiple point in which gradient fields are generated, i.e. dielectrophoretic effects occur). This is the first direct visual evidence of multigradient dielectrophoresis under conditions typical of CEC at the length scales disclosed herein. CEC is typically conducted in about 20 to about 300 μm inner diameter capillaries of about 5 to about 50 cm lengths and about 5 to about 30 kV are applied across these capillaries so field strength varied from about 6 kV/mm to about 10 V/mm.

Figure 4:
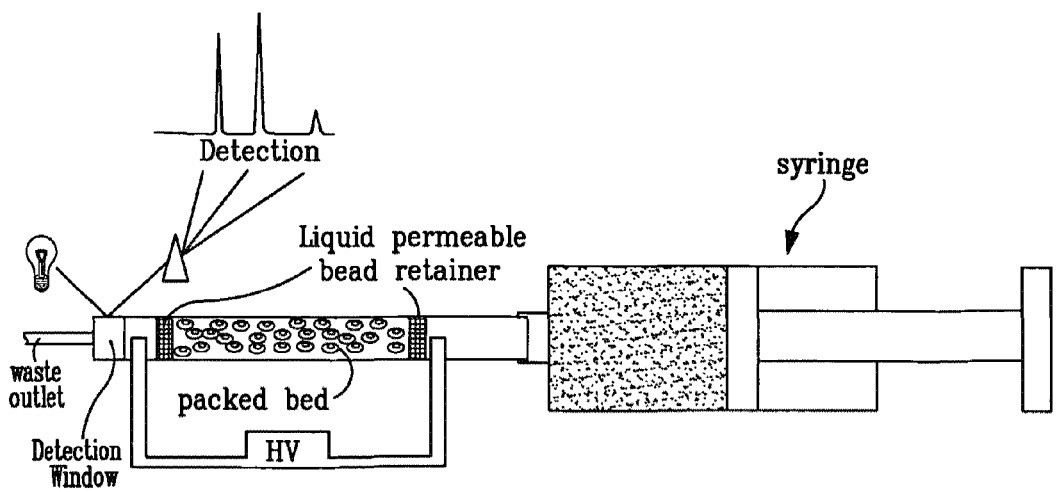
FIG. 4 schematically represents the device employed for testing nanodielectrophoresis and dielectrokinetic chromatography according to the present invention. Fused silica capillaries (or PEEK cartridges) were randomly packed with various microspheres on 1 to 3 cm length to generate multipoint (multigradient) non-linear electric fields upon application of voltage potentials.

FIG. 4 schematically shows a capillary, such as a fused silica capillary, packed with perturbers, e.g. polystyrene microspheres. For the capillary embodiment shown in FIG. 4, DEKC separation and manipulation of analytes depends on the geometry, the relative size of the packed perturbers, the packing porosity and the magnitude of the applied voltages. For example, perturbers having about 20 μm diameters are able to dielectrophoretically trap analytes of smaller diameters, or trap at lower voltages than perturbers having about 45 μm diameters. Those skilled in the art may readily select sizes and shapes of perturbers and voltages suitable for separating a given analyte in accordance with the present invention.

To assay analytes having small diameters such as cells, e.g. *Bacillus subtilis* spores, a 2 cm long 100 μm ID capillary packed with 20 μm polystyrene microspheres purchased from Bangs Laboratories (Fishers, Ind.) was employed. The small 20 μm polystyrene microspheres, however, made visualization of the trapped analytes challenging due to the diminished size of the spaces between the perturbers where rarefaction was observed in previous experiments. Therefore, a capillary was packed at high pressure (600 psi) in order to tightly wedge the perturbers into the capillary after which part of the packed bed was removed as liquid was flowed through the capillary. In this way it was possible to visualize the flow of analyte particles directly following the packed bed.

Figures 5A, 5B:
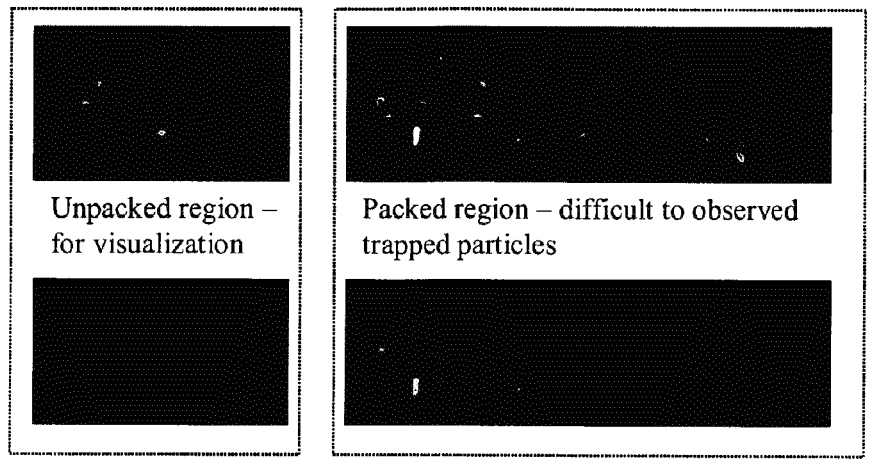
FIG. 5A shows trapping of fluorescently labeled *Bacillus subtilis* spores in a 100 µm ID fused silica capillary packed with 20 µm polystyrene microspheres in the presence of an electric field of about 50 V/mm. Trapping occurs in the upper image as voltage is applied, although it is difficult to observe through the packed region.
FIG. 5B shows the release of fluorescently labeled *Bacillus subtilis* spores was achieved in the open section (does not contain packed perturbers) of the capillary.

FIG. 5A shows trapping and release of fluorescently labeled *Bacillus subtilis* spores in a 100 μm ID fused silica capillary packed with 20 μm polystyrene microspheres (Bangs Laboratories, Fishers, Ind.) in the presence of an electric field of about 50 V/mm. Under the influence of the applied voltage, the spores were trapped in the packed region (top image). Due to the small size of the perturbers, the rarefaction and trapping of spores it is difficult to observe in the top image of FIG. 5A. When the voltage dropped to zero, as shown in the bottom image of FIG. 5A, the concentrated spores were released from the packed section. FIG. 5B shows the open section (does not contain packed perturbers) of the capillary. While essentially no spores are observed in the open section of the capillary during trapping (top image), a bright plume of spores corresponding to the release of fluorescently labeled *Bacillus subtilis* spores was observed as voltage was dropped to zero (bottom image).

Figure 5C:
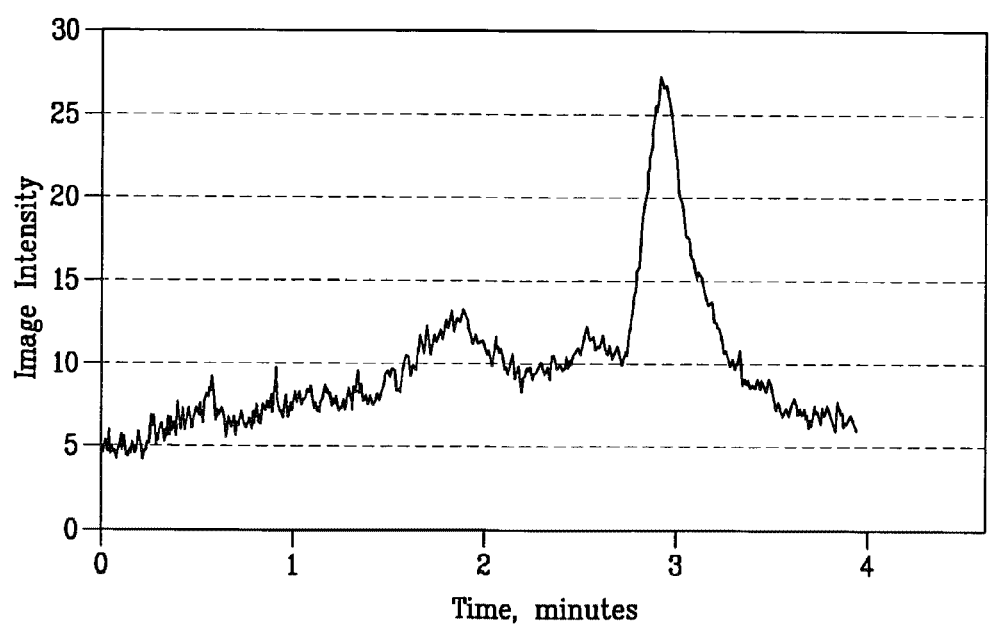
FIG. 5C shows the concentration and release of fluorescently labeled *Bacillus subtilis* spores in a 2 cm long capillary packed with 20 µm polystyrene microspheres. Gradual trapping of spores at electric fields of about 50 V/mm is followed by a release of captured spores when applied voltage is dropped to zero.

FIG. 5C is a graph showing the variation in fluorescent intensity of the open capillary area that is not packed with 20 μm microspheres during the DEP experiment and includes DEP trapping (very low signal in the first two minutes when voltages is applied because the fluorescent perturbers do not exit the packed bed) and the release of trapped analytes (when voltage is no longer applied over the following two minutes and the flow field was stopped). The graph was generated using image processing software that integrates the brightness of the selected areas of the video frames as a function of time. The tall peak in FIG. 5C corresponds to the concentrated plug of spores released from the packed perturbers when the DEP flow field was stopped.

Three different particles, (1) semi-soft organic polymer microspheres (dextran based), (2) rigid organic polymer microspheres (polystyrene and methacrylate) and (4) silicate microspheres were used as the perturbers for DEKC separations described herein. The bead sizes were selected based on ease of packing in capillaries, size distribution, commercial availability and cost. Those skilled in the art, however, may readily select a perturber size based on its suitability or its optimization for a desired analyte to be assayed. Polystyrene microspheres of 20, 70 and 90 μm diameters, 20 μm borosilicate microspheres, and 70 μm dry soda lime microspheres were purchased from Duke Scientific (Microgenic Corporation, Fremont, Calif.). A kit of polystyrene microspheres of 0.5 μm, 1 μm, 45 μm and 90 μm diameters was purchased from Bangs Laboratories (Fischer, Ind.). Glass microspheres with diameters ranging from 30 μm to 50 μm and 105 μm to 150 μm were purchased from Polysciences, Inc. (Warrington, Pa.).

Carboxylate-modified microspheres (e.g. FLUOSPHERES® obtained from Molecular Probes Inc., Eugene, Oreg., a division of Invitrogen Inc., Carlsbad Calif.) were employed as the perturbers in the initial study of the dielectrophoretic effects. The carboxylate-modified microspheres are latex-based spheres that have carboxylated surfaces and are derivatized with a yellow-green fluorescent dye. Packings of 100 nm, 500 nm, 1 μm and 2 μm carboxylate-modified microspheres were employed. Before use, the microspheres were diluted 1:1000 in a running solution (DI water with pH adjusted to 8.0 using 10 mM NaOH, and 0.1% vol PLURONIC® (BASF Chemicals) surfactant (a copolymer of ethylene oxide and propylene oxide).

Microspheres of 20 μm to 100 μm were packed in polytetrafluoroethylene coated fused silica capillaries with 360 μm outer diameter (OD) and inner diameters (ID) ranging from 75 μm to 150 μm using the procedure described in detail by Chirica et al. (Electrophoresis, 2000, v. 22:56, which is herein incorporated by reference).

Figure 6A:
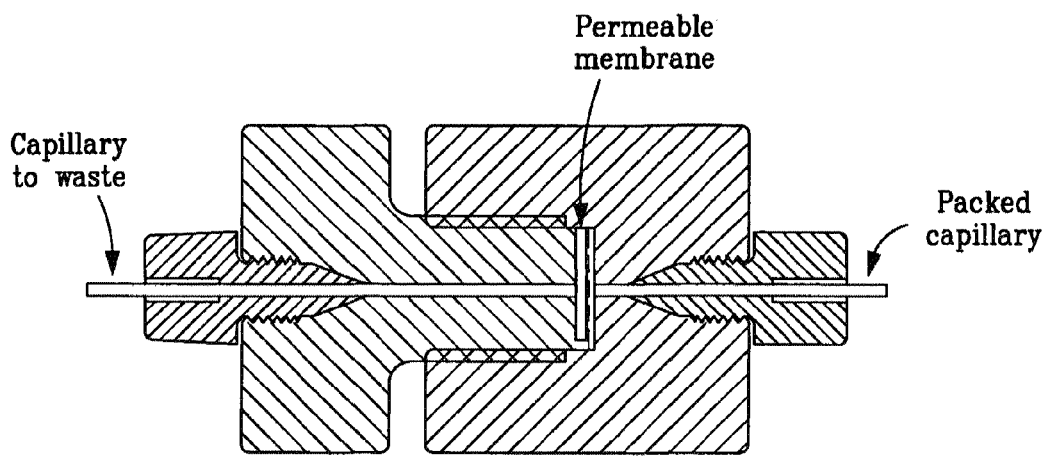
FIG. 6A schematically shows a first embodiment of a polyetheretherketone (PEEK) thermoplastic fitting which connects the perturber section (the "packed capillary") with another capillary to the left ("capillary to waste") to enable on-line, low dispersion flow and rapid connection to waste or detection devices. The fitting is designed to accommodate a permeable membrane which allows unperturbed flow of larger size particulates (such as spores, cells, macromolecules) while retaining the packed perturbers.

Two challenges were overcome with two modifications to the Chirica et al. method. First, the polytetrafluoroethylene coated fused capillaries are extremely fragile; therefore, to prevent breakage they were not sonicated during packing. Second, secondary effects that might occur as nanometer-sized analytes are passed through the irregular structure of the frit needed to be eliminated; therefore, a new polyetheretherketone (PEEK) thermoplastic fitting in which the microspheres are retained within the capillary by polyether membranes (Spectrum Laboratories, Rancho Domingues, Calif.) fixed in between two sealing surfaces was designed and used. FIG. 6A schematically shows a first embodiment of the PEEK fitting. The capillary is firmly mounted against one side of the PEEK fitting, while the other side is connected to a second capillary tubing which allows liquid flow towards waste or to a diction device. During packing and operation the fitting effectively immobilizes microspheres/perturbers with diameters larger than the opening of the membrane, while allowing smaller analytes to pass through This fitting addresses the specific experimental requirements of manipulating particulates in the form of analytes (biological analytes such as cells, spores, viruses, macromolecular complexes) and perturbers in capillary/micrometer-size format with essentially no retention or non-specific interactions and minimal band broadening. The size of the concentrated plug can thus be preserved during routing towards other modules for further processing, detection, etc.

Figure 6B:
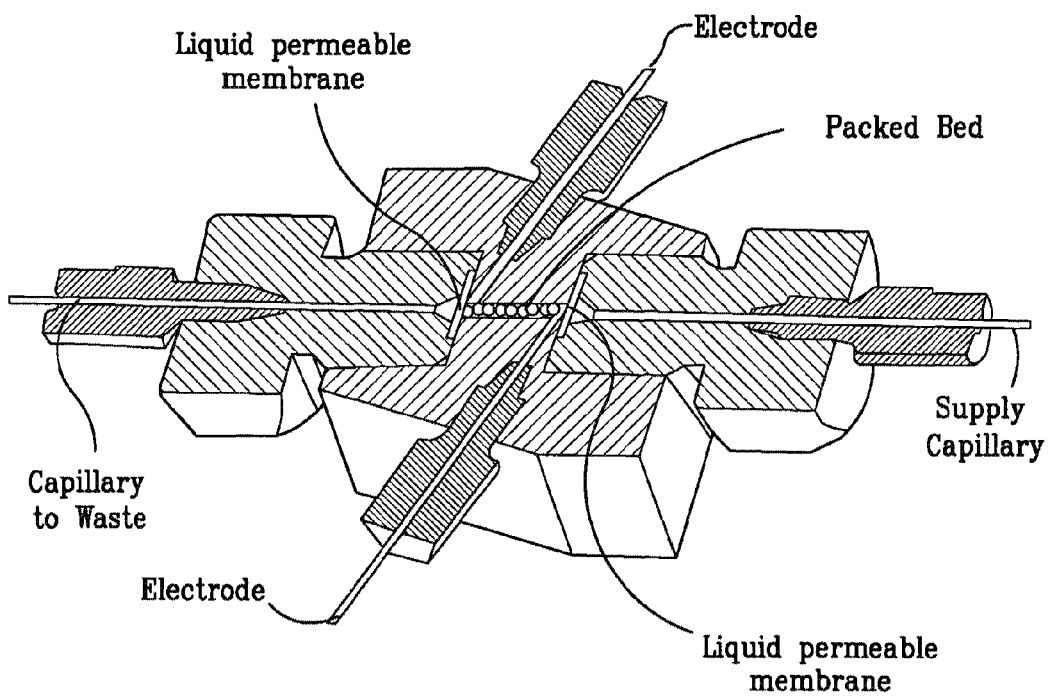
FIG. 6B schematically shows a first embodiment of a PEEK thermoplastic fitting which comprises a packed column sandwiched between two liquid permeable membranes within a central body, two off-axis fittings for introducing/inserting electrodes into the region of the packed bed adjacent to each membrane; and two axial fitting for holding a supply and a waste capillary line.

The internal volume of the second embodiment of the PEEK cartridge depicted in FIG. 6B is defined by a sandwich of polyester membranes (Spectrum Laboratories, Rancho Dominguez, Calif.) mounted firmly between one flat bottom assembly and the main body. The variable internal packing volumes (1-100 µl) were readily packed against the first mounted membrane using a laboratory vacuum line (20 in. Hg vacuum). The perturbers packed in the PEEK cartridge gives well over 2,000 points which provide steep electric field gradients when a voltage is applied to the cartridge, thereby providing a substantial increase in sample capacity and the size of analytes that can be manipulated using electrokinetic and DEP field gradients.

Rapid packing (less than about 2 minutes) ensured homogeneous beds without voids or channeling, thereby minimizing redistribution of the perturbers and improving the lifetime of the PEEK cartridge. At a vacuum of 20 in. of Hg no bed deformation occurred, which is of particular significance when packing compressible gel perturbers. The second membrane and the second flat bottom assembly were then mounted. The two membranes confined the perturbers while allowing liquid to flow through the bed. In addition, the PEEK cartridge was easily emptied and refilled with desired packing, thereby substantially reducing cost. The PEEK fittings and three-way microvalves (Sandia National Laboratories, Livermore, Calif.) enable direct connection of the PEEK cartridge to a microliter size exclusion chromatography (µl-SEC) cartridge and to a 50 µm inner diameter (ID), 360 µm outer diameter (OD) polyimide-coated fused silica capillaries (Polymicro Technologies, Phoenix, Ariz.). The direct connection ensures zero dead volume within the cartridge and interconnects.

Figure 7:
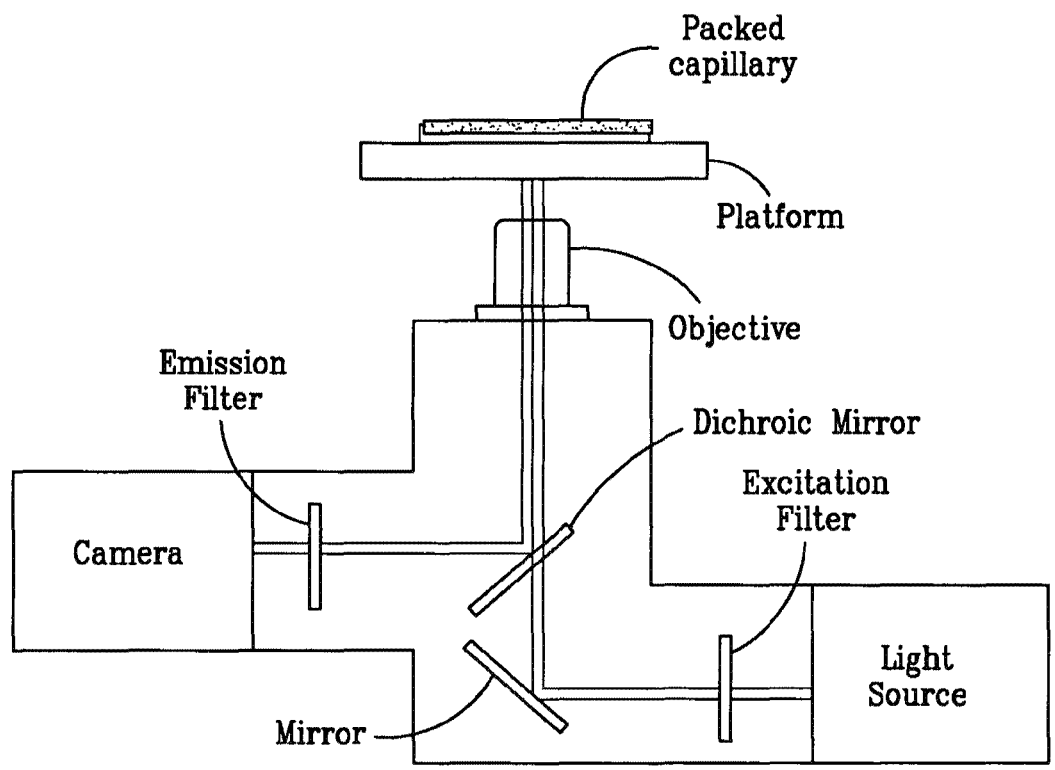
FIG. 7 schematically shows the fluorescence inverted microscope, light source and video camera used to observe and record the dielectrokinetic chromatography experiments disclosed herein.

In the DEKC experiments herein, a glass syringe (Hamilton, Reno, Nev.) was mounted on a pump (Cole Palmer, Vernon Hills, Ill.) and connected it to a pressure transducer and then to the PEEK cartridge (1.5 mm dia., 50 mm long) packed with perturbers. The manipulation of cells and analytes were observed and recorded using a fluorescence inverted microscope, light source and video camera in the setup depicted in FIG. 7. Methods and devices known in the art may be used for image processing and collection. The absorbance of the fluid eluted from the PEEK cartridge was analyzed using a commercially available UV detector with capillary flow-cell. After each use, the PEEK cartridge was cleaned and re-conditioned.

Generally, the voltage applied to the PEEK cartridge ranged from about 2000 to about 4000 V which resulted in local rarefaction of analytes in the space between the perturbers (e.g. microspheres); the analytes were concentrated at or near the surfaces of the microspheres at points of steep field gradients.

The sample was continuously supplied to the DEP device using a Hamilton syringe (Hamilton, Reno, Nev.) connected to a Cole-Parmer syringe pump (Cole Parmer, Vernon Hills, Ill.). Other methods and devices for providing a suitable hydrodynamic flow known in the art may be readily implemented by those skilled in the art.

Figure 8A:
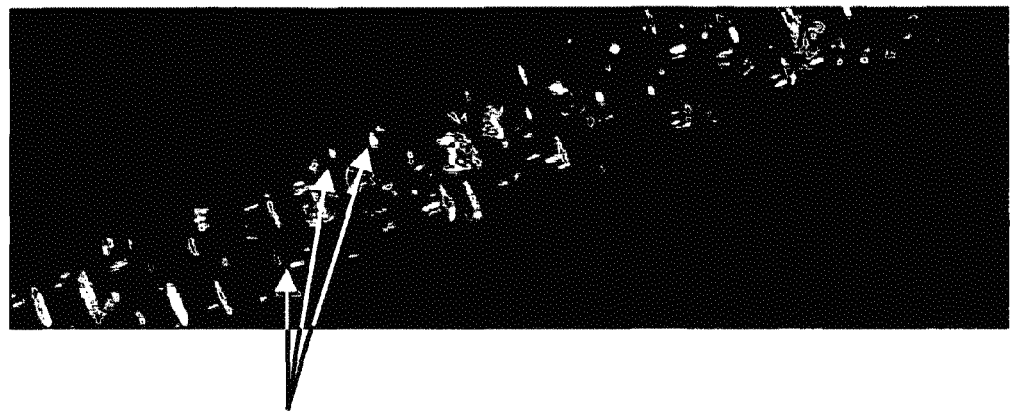
FIG. 8A shows 1 µm fluorescently labeled analytes trapped due to the non-uniform field gradient generated by 45 µm microspheres packed in 2 cm long capillaries at field strength of about 45 V/mm.
Figure 8B:
FIG. 8B shows the release of the 1 µm fluorescently labeled analytes of FIG. 8A.

FIG. 8A shows the trapping of microspheres in the field gradients generated by the packed bed of 45 µm diameter microspheres purchased from Bangs Laboratories (Fischer, Ind.) in a capillary column under an applied voltage. Almost immediately after the electric field was applied, the DEP and drag force on the perturbers situated close to the high field regions were balanced and the observed net effect was trapping of analytes (carboxylate-modified microspheres) in a fluid sample. Analytes far from the high gradient field region continued to travel until they encountered one and they were trapped. The electric fields were applied for about 1 minute. When the voltage potential was dropped to zero, the trapped analytes were released in a concentrated plug as shown in FIG. 8B. Because of the substantially straight capillary, little to no diffusion of the concentrated plug was observed, thereby significantly increasing the overall sensitivity of detection as compared with prior art DEP devices.

Aside from the non-uniform field generation and the nature of the analytes, the composition of the suspending medium has an impact on analyte movement due to DEP flow fields. As stated in the Clausius-Mossotti factor, alteration of conductivity and permittivity of the suspending medium can be used to optimize the DEP flow fields and enhance selectivity in discriminating between different analytes. Higher conductivity of the solutions in which the perturbers are suspended cannot only diminish the DEP flow fields, but change the direction of the field forces from positive to negative. In fact, a significant variation in the magnitude of DEP flow fields was observed between a DI solution and a dilute NaOH (pH 8.5) solution.

Nanoscale Dielectrokinetic Chromatography (nanoDEKC)

As provided herein, various chromatographic media were examined for their suitability in DEKC separations of nanoscale analytes (nanoDEKC). The chromatographic media examined is set forth in Table 1 as follows:

TABLE 1

Properties of Chromatographic Medium for DEKC

| Chromatographic Medium | Composition | Diameter µm* | MW Cutoff kDa* | Pore Size Å* |
|---|---|---|---|---|
| Bio-GEL P-6 | Polyacrylamide gel | <45 | 6-40 | NA |
| SEPHADEX G-25 | Carboxyhydrate gel | 20-80 | 1-5 | NA |
| TSK-GEL SW | Hydrophilic layer coated silica | 10 | NA | NA |
| TOYOPEARL HW-40S | Methacrylate polymer | 20-40 | 0.1-10 | 50 |
| TOYOPEARL HW-40F | Methacrylate polymer | 30-60 | 0.1-10 | 50 |
| TOYOPEARL HW-40C | Methacrylate polymer | 50-100 | 0.1-10 | 50 |
| TOYOPEARL HW-65S | Methacrylate polymer | 20-40 | 40-5000 | 1000 |

*sizes are approximate. For example "<45" should be read as "less than about 45" and "20-80" should be read as "about 20 to about 80"

Figure 9:
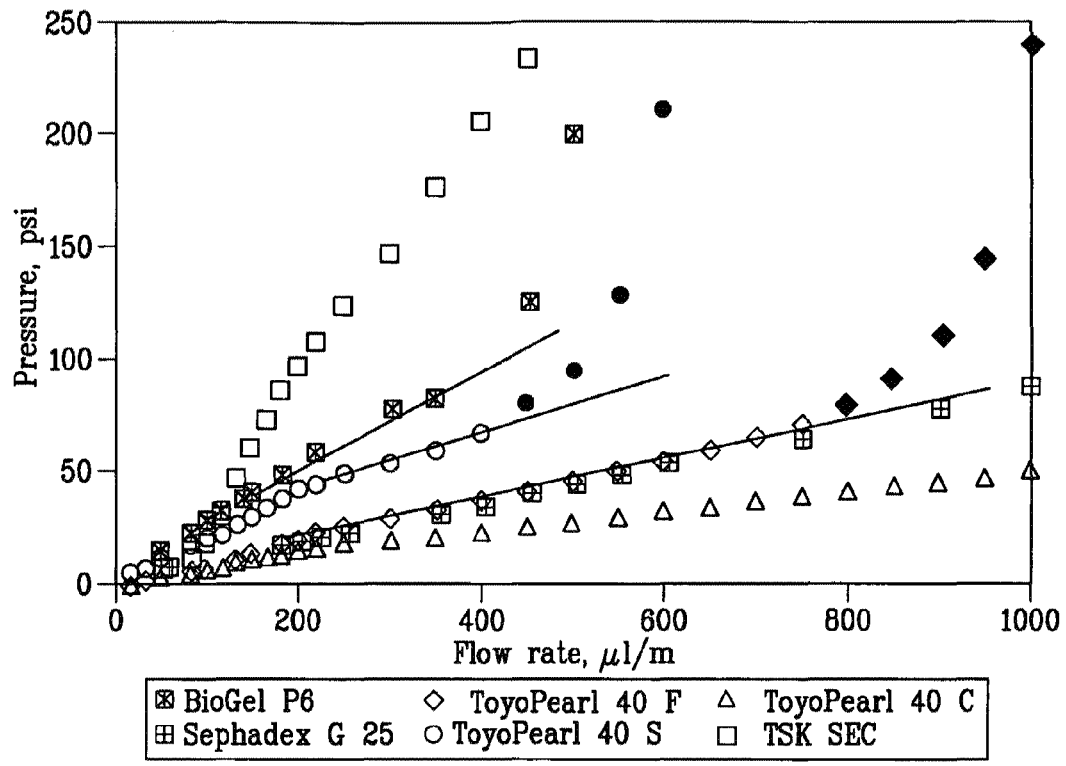
FIG. 9 shows the flow rate dependence on applied pressure using PEEK cartridges.

To characterize the chromatographic media packed in the PEEK cartridges described herein, flow rate dependence on applied pressure was monitored using methods known in the art. FIG. 9 is a graph of the results.

Where a chromatographic medium behaves as an incompressible porous solid, the flow rate has a linear dependence to pressure, which is consistent with Darcy's law:

$$Q = \Delta p K \left(\frac{A}{\eta L}\right), \quad \text{(Equation 1)}$$

where Q is the flow rate, $\Delta p$ is the difference between applied pressure and exit pressure, $\eta$ is the viscosity of the mobile phase, L is the length of the column, $A=\pi_c^2/4$ is the cross-section of the cartridge, $d_c$ is the diameter of the cartridge and K is a proportionality constant, which is inversely proportional to the permeability of the bed. Using Darcy's law, one can estimate K from monitoring the flow rate dependence on applied pressure. Most importantly, this data reveals the conditions in which a chromatographic medium is incompressible and, therefore, behaves reproducibly.

SEC columns using each of the resins listed and described in Table 1 where prepared and tested. Based on the linear plots in FIG. 9, the proportionality constants for these resins were determined to be: TSK SEC=about $972 \times 10^{-8}$ mm$^2$; BioGel P6=about $563 \times 10^{-8}$ mm$^2$; Sephadex G 25=about $215 \times 10^{-8}$ mm$^2$; ToyoPearl 40S=about $430 \times 10^{-8}$ mm$^2$; ToyoPearl 40F=about $205 \times 10^{-8}$ mm$^2$ and ToyoPearl 40C=about $153 \times 10^{-8}$ mm$^2$. Above about 70 psi, a change in permeability was observed for BioGel P6, ToyoPearl 40S and ToyoPearl 40F—a slight increase in flow rate caused an exponential increase in pressure. Data points corresponding to the exponential increase in pressure are marked with shaded data points in FIG. 9. Thus, about 70 psi is the threshold value over which substantial compression of the whole packed bed occurs for BioGel P6, ToyoPearl 40S and ToyoPearl 40F.

For soft gels and/or small diameter, highly porous perturbers, the optimum operating domain is limited to lower flow rates. FIG. 9 shows that all the chromatographic media investigated, with the exception of TSK SEC, follow the ideal flow rate to pressure dependence at pressures smaller than about 60 psi and flow rates less than about 200 µl/min. In the linear regime, the chromatographic media exhibited reproducible behavior in measurements of the slopes of pressure/flow rate curves. The pressure readings for consecutive pressurization experiments varied by about 1% relative standard deviation for the same PEEK cartridge and less than about 5% relative standard deviation between different PEEK cartridges.

As shown in FIG. 9, the TSK SEC chromatographic medium was found to be very different to that of the previously examined chromatographic media. Silica-based TSK SEC microspheres have a smaller diameter (10 µm) and form a considerably less permeable bed, i.e. pressure increases greatly with small increase in flow rate. See FIG. 9. The incompressibility of silica TSK SEC microspheres offers the advantage of extending the optimum operating range to higher pressures. However, low-pressure operation is not only suitable for the majority of microfluidic systems, but also preferred in portable systems due to the large size of high pressure pumps. High backpressures associated with small diameter silica packing limits the column length. We were able to vacuum-pack and test 1.5 mm diameter cartridges of only 15 mm long; the reduction in total packing volume significantly reduced the sample capacity of the column. In addition, silica-based packings are less stable at pH 9.0, the pH of the desired exchange buffer (effective fluorescamine labeling and reproducible CGE separations occur at pH 9.0).

The comparison between the experimental value for the proportionality constant, calculated from the slopes of the linear regime in the pressure/flow rate curves, and the theoretical value, calculated for packed beds of solid spheres, provides information on the structure of the packed bed during operation. For example, the experimental value of the proportionality constant K in the case of PEEK cartridges packed with the soft resin Sephadex G 25 was estimated to $215 \times 10^{-8}$ mm$^2$. Using Kozeny-Carmen equation, commonly used for packed beds of spheres, the theoretical value of the proportionality constant K is calculated as follows:

$$K = \frac{d_p^2}{180} \frac{\varepsilon^3}{(1-\varepsilon)^2}, \quad \text{(Equation 2)}$$

where $d_p$ is the diameter of the packing and E is the void fraction. If a void fraction of about 0.4 and an average particle diameter of about 45 µm is assumed, the calculated K values for Sephadex G 25 beds is about $215 \times 10^{-8}$ mm$^2$. The agreement between the theoretical and experimental K values indicates that, within the optimal operating domain, a PEEK cartridge packed with soft size exclusion perturbers has a rigid structure which is also suitable for generation of predictable and reproducible dielectrophoretic interactions.

Separation of Viruses and Proteins

The chromatographic media in Table 1 were used successfully in the cartridge embodiment illustrated in FIG. 6B for the on-line hydrokinetic separation of intact T2 bacteriophages from low molecular weight components, such as salts and peptides, in fluid samples. Since the PEEK cartridges incorporate replaceable membranes, one may readily employ a membrane with a desired pore size to be used in conjunction with a selected chromatographic medium. For example, perturbers of about 30 µm diameter or higher and a nylon membrane having about a 10 µm mesh size (Spectrum Laboratories, Rancho Dominguez, Calif.) was used herein. One skilled in the art may readily select a membrane having characteristics suitable for a given application. For example, for assaying viruses, such as bacteriophages, a membrane having a pore size which allows viruses and viral components, but not bacteria, to pass through to the chromatographic media may be readily selected by those skilled in the art.

Figure 10:
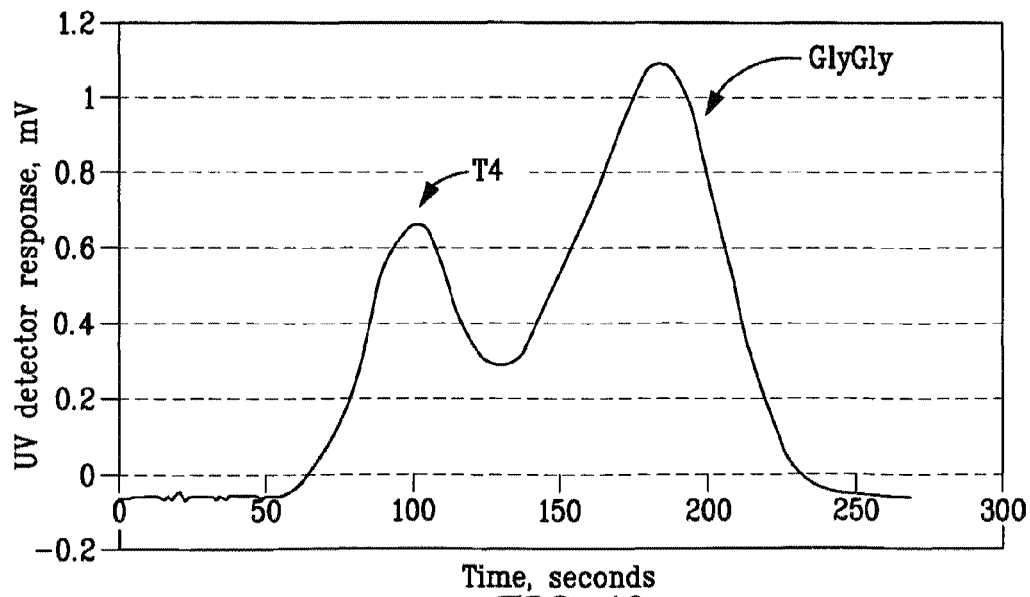
FIG. 10 depicts the separation of a microliter-volume sample of T2 bacteriophages from GlyGly achieved in a cartridge packed with ToyoPearl HW 65 chromatographic medium.

FIG. 10 depicts the separation of a microliter-volume sample of T2 bacteriophages from GlyGly achieved in a cartridge packed with ToyoPearl HW 65 chromatographic medium. The analytes were resolved in less than about 5 minutes. Superposition of dielectrokinetic effects dictated by the overall size of the perturbers/packing over the size-exclusion effects dictated by the porosity of the packing enables separation of bio-particulates (such as bacteriophages, spores) affected/trapped by dielectrophoresis (as described in previous experiments) from macromolecular complexes, such as protein complexes, which are separated by size exclusion, but are too small to be influences by dielectrophoresis.

Adsorption of Analytes on Chromatographic Media

As various suspension media will exhibit different ionic strengths, pH values, and chemistries, which have an effect on adsorption of analytes on chromatographic media, the following experiments were conducted to demonstrate the compatibility of our system with chromatographic separations of bio-particulates.

Selective adsorption of T-even bacteriophages determined by the composition their coat proteins was examined with various chromatographic media. The challenge was to determine the interaction chemistry that allows for rapid kinetics for complete retention as well as complete release of microorganisms when conditions are changed. A specific requirement for this application is that the loading and elution solvents need to be compatible with the organisms; more specifically, they should not cause premature lysing and or aggregation of the microorganisms The retention and release of T2 and T4 bacteriophages by hydrophobic chromatographic media having ethyl, butyl, hexyl, or phenyl moieties grafted on polymer supports of 50 µm diameter was tested. Since aqueous solutions of T4 absorb UV radiation, we were able to monitor the breakthrough curve for retention and release. Incomplete retention of T4 bacteriophages by polymeric-based materials was observed. This is probably due to the reduced surface coverage of the polymeric methacrylate material with highly hydrophobic moieties. By overlapping the dielectrophoretic dimension on the incomplete hydrophobic retention, one can trap the bacteriophages near the packing, which act as perturbers and, therefore provide a significant increase in the retention of the bacteriophages. Meanwhile, particulates that do not interact with these supports, such as viruses, spores with hydrophilic coat proteins, are not affected by the dielectrophoretic trapping and can therefore be separated from larger-size bacteriophages.

Figure 11:
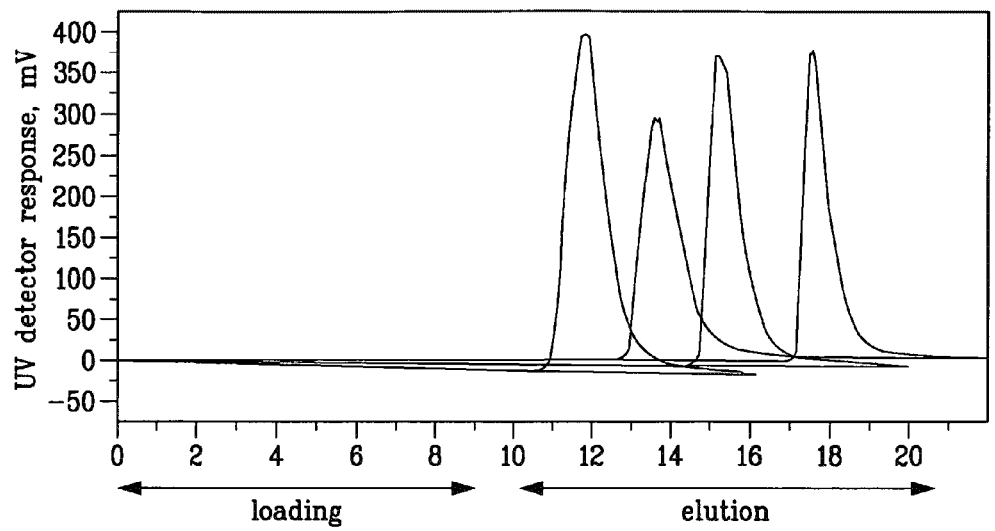
FIG. 11 illustrates the viral peaks obtained in 4 consecutive experiments comprised of a solution of about $10^8$ viruses/ml was loaded for about 9 minutes at a flow rate of about 30 µl/min on a 30 µl PEEK cartridge packed with ToyoPearl DEAE 650S anion exchange material.
Figure 12:
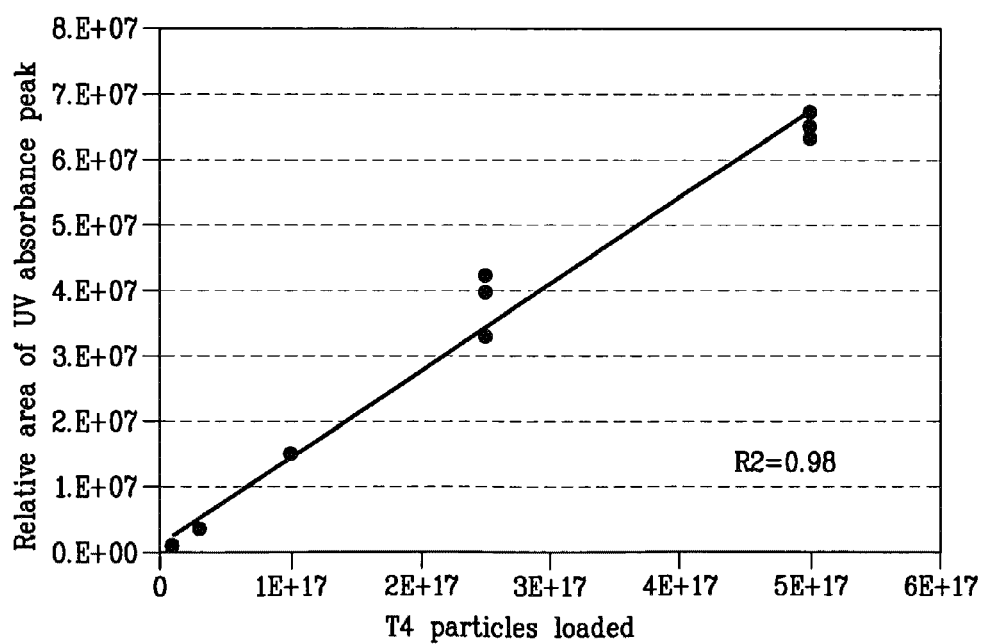
FIG. 12 demonstrates that the method of FIG. 11 can be used for quantitative retention of T4 with high sample capacity.

Another type of chromatographic media, ToyoPearl DEAE 650S, which relies on ionic interactions as the retention mechanism provided reproducible interactions between viruses and the solid support. In particular, anion exchange retention of T4 viruses occurred at a pH of about 8 and low ionic strength conditions. A solution of about $10^8$ viruses/ml was loaded for about 9 minutes at a flow rate of about 30 µl/min on a 30 µl PEEK cartridge packed with anion exchange material ToyoPearl DEAE 650S. Upon addition of elution solvent (200 mM NaCl) at a flow rate of about 10 µl/min, the viruses were released from the packed bed and the corresponding absorbance was recorded. FIG. 11 illustrates the viral peaks obtained in 4 consecutive experiments. More significantly, we demonstrated that the method can be used for quantitative retention of T4 with high sample capacity. See FIG. 12.

Microspheres with a wide range of sizes (nanometers to hundreds of microns), geometries (spherical and irregularly shaped), porosities, conductivities and surface functionalities are commercially available and can be used for dielectrokinetic chromatographic separations of micrometers and nanometer-size analytes. Companies that commercialize such microspheres include: Macherey Nagel (River Vale, N.J.), Tosoh Biosciences (Montgomeriville, Pa.), Bangs Laboratories (Fishers, Ind.), Duke Scientific (Microgenic Corporation, Fremont, Calif.), Waters (Milton, Mass.), Agilent Technologies, Inc. (Santa Clara, Calif.), and the like.

Porous monoliths or sol gels which may be synthesized in situ are known in the art and may likewise be used as perturbers according to the present invention. See e.g. Svec et al. *Monolithic Materials Preparation Properties and Applications,* 2003, Elsevier (Publisher), Amsterdam.

Those skilled in the art may readily modify or select buffer compositions to optimize the field strength, gradient steepness and/or flow velocity and thereby result in dielectrophoretic trapping and/or competitive chromatographic retention for a given application. For example, the use of organic solvents in the buffer decreases conductivity while affecting chromatographic behavior; salts present in the buffer can increase conductivity while enhancing hydrophobic interaction and decreasing ion exchange interaction; haptenes present in the buffer have minimal effect on conductivity while significantly influencing interactions between biomolecules, such as glycosyl groups with lectins-immobilized perturbers, and the like.

A variety of DEKC formats are contemplated herein. Specifically, various chromatographic methods known in the art, such as reverse phase, immuno-chromatography, ion exchange, chromatofocusing, size exclusion, and the like, as well as operational alternatives (isocratic versus gradient) may be combined with DEP trapping to result in a DEKC format in accordance with the present invention. For example, a microchannel may be packed with perturbers having a desired lectin surface chemistry to give a perturber section according to the present invention. Under an applied field, glycosylated molecules (analytes) will be dielectrophoretically trapped (mostly based on the size of the molecules) and the lectin surface chemistry will trap and retain the analytes by affinity chromatography. In another example, dielectrophoretic trapping and streaming enhances chromatographic retention on materials with surface chemistries enabling ion exchange interactions (such as alkylamines, etc). Chromatographic retention of dielectrophoretically trapped analytes may be readily optimized by those skilled in the art by varying the pH of the mobile phase.

In some embodiments, the methods and devices of the present invention may be combined or complexed with filtration and other separation methods known in the art.

Dielectrophoresis is a phenomenon that acts on a certain volume of fluid in which the electric field gradient is high enough to affect a given particulate. Chromatography is a surface effect which relies on the direct interaction/attraction between analytes and the surface of the perturbers. By combining these two orthogonal techniques (techniques which act through independent mechanisms) in the same setup, on the same sample one can substantially improve the number of species that can be separated. For example, to separate the components of a sample which contains bacteriophages, viruses and molecular contaminants (such as, detergents, urea, etc), one can employ particulates/perturbers with 30-50 µm sizes which in our setup at 50 V/mm can trap bacteriophages. The chemistry of such perturbers is chosen such to cause the surface retention of the viruses while inert to the specific molecular contaminant (for example hydrophobic, ionic-exchange or glucosaminoglycan (GAG)-material). The sample can be passed through the capillary/cartridge packed with these perturbers while voltage is applied at 50 v/mm. As a result, the bacteriophages are dielectrophoretically trapped, while dielectrophoresis has no effect on the viral particles or sample contaminants in a setup with 40-50 µm diameter perturbers. The viruses are chromatographically retained while the contaminants flow through the packed cartridge/capillary un-retained. To separate the bacteriophages from viruses one can vary the composition of the fluid flowing through the cartridge: for example, if a hydrophobic material was used one can increase the percentage of methanol to cause viral desorption. Similarly, if the perturbers have surfaces which favor ion-exchange interactions, one can change the pH or the salt content of the fluid to desorb the viruses. In the case of GAG-immobilized materials, viral elution occurs at specific sulfate disaccharides. As the change in fluid composition occurs while voltage is still applied and the bacteriophages are dielectrophoretically trapped, this method effectively concentrates bacteriophages and viruses, while removing the contaminants.

Increased separation power is particularly needed in complex samples such as bodily fluids (blood, serum, urine, etc.). By using GAG-perturbers with diameters of 20 µm or lower dielectrophoresis can be used to trap viruses. One can select a specific GAG functionality to favor retention of one virus versus another. Dielectrophoresis traps both viruses and removes potential contaminants as the sample is injected in our setup. A change in the fluid composition contain specific sulfate disaccharides will elute virus one while the other(s) are still trapped. A similar experiment can be envisioned when using lectin-immobilized perturbers to differentiate between species with different glycan structures.

In some embodiments, the DEKC devices and methods disclosed herein may be used for electroporating or lysing cells and membranes. See Wang et al. Analytical Chemistry, 2006, v. 78:5158-5164, which is herein incorporated by reference in its entirety. For example, lysis and electroporation may readily be achieved using the methods and devices of the present invention by increasing the applied field or by using perturbers with sharp edges to generate highly localized (within about 10 nm) steep electric field gradients. In these "hot spots" (areas of steep electric field gradients) electropermeation and/or electrolysis of cells and/or membranes is achieved during or following trapping by DEKC.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A device microfluidic device, comprising:

a microfluidic channel comprising an inlet and an outlet;

at least one perturber section comprising a plurality of randomly arranged perturber bodies disposed within a portion of the channel; and a high voltage power supply for applying an electrokinetic flow field and a dielectrophoretic flow field within the channel;

wherein the dielectrophoretic flow field interacts with the plurality of randomly arranged perturber bodies to produce at least one field non-uniformity within the perturber section, and wherein the at least one field non-uniformity operates to trap and concentrate an analyte within a section of the section of the channel.

2. The device of claim 1, wherein the high voltage power supply is a power supply operable to supply an applied voltage from about 2000 V to about 4000 V.

3. The device of claim 1, wherein the perturber bodies are the same or different.

4. The device of claim 1, further comprising a plurality of perturber sections, wherein two or more perturber sections are arranged in series or parallel.

5. The device of claim 4, wherein a plurality of perturber bodies in a first perturber section are the same as or different from a plurality of perturber bodies in a second perturber section.

6. The device of claim 1, wherein the perturber bodies comprise a solid body, a porous body, or a solid body having a porous outer layer.

7. The device of claim 1, wherein the perturber bodies comprise spheres, rods, regular structures, or irregular structures.

8. The device of claim 1, wherein the perturber bodies comprise silica, borosilicate glass, methacrylate, polyacrylamide, polystyrene divinylbenzene, dextrose, latex, metal, metal oxide, or ceramic, or a combination thereof.

9. The device of claim 1, wherein the analyte comprises a detectable species.

10. The device of claim 9, further comprising a light absorbance detector for detecting the detectable species.

11. The device of claim 1 further comprising a reaction area configured to identify a protein or a gene sequence.

12. The device of claim 1, further comprising liquid permeable membranes, wherein the at least one perturber section is disposed between the membranes.

* * * * *